United States Patent
Olson

(10) Patent No.: US 10,278,858 B2
(45) Date of Patent: May 7, 2019

(54) OPHTHALMIC SURGICAL DEVICE WITH ADJUSTABLE FILAMENT AND METHOD OF USE

(71) Applicant: THE REGENTS OF THE UNIVERSITY OF COLORADO, A BODY CORPORATE, Denver, CO (US)

(72) Inventor: Jeff Olson, Denver, CO (US)

(73) Assignee: The Regents of The University of Colorado, A Body Corporate, Denver, CO (US)

( * ) Notice: Subject to any disclaimer, the term of this patent is extended or adjusted under 35 U.S.C. 154(b) by 451 days.

(21) Appl. No.: 14/423,936

(22) PCT Filed: Aug. 26, 2013

(86) PCT No.: PCT/US2013/056573
§ 371 (c)(1),
(2) Date: Feb. 25, 2015

(87) PCT Pub. No.: WO2014/035862
PCT Pub. Date: Mar. 6, 2014

(65) Prior Publication Data
US 2015/0257927 A1    Sep. 17, 2015

Related U.S. Application Data

(60) Provisional application No. 61/694,084, filed on Aug. 28, 2012.

(51) Int. Cl.
*A61F 2/16* (2006.01)
*A61F 9/00* (2006.01)
(Continued)

(52) U.S. Cl.
CPC ...... *A61F 9/0008* (2013.01); *A61B 17/32056* (2013.01); *A61B 18/082* (2013.01);
(Continued)

(58) Field of Classification Search
CPC ............... A61F 9/0008; A61F 9/00736; A61F 9/00821; A61F 9/00727; A61F 9/007;
(Continued)

(56) References Cited

U.S. PATENT DOCUMENTS 798,839 A      9/1905   Stowe
4,246,902 A *  1/1981   Martinez .............. A61F 9/00763
                                                         604/22

(Continued)

FOREIGN PATENT DOCUMENTS

FR    2655836       6/1991
JP    62192725     12/1987
(Continued)

OTHER PUBLICATIONS

International Search Report and Written Opinion dated Nov. 18, 2013 in Application No. PCT/US2013/056573.
(Continued)

*Primary Examiner* — Jocelin C Tanner
(74) *Attorney, Agent, or Firm* — Snell & Wilmer L.L.P.

(57) ABSTRACT

An ophthalmic surgical device in accordance with various embodiments of the present disclosure comprises an elongate element and a filament. The device may further comprise one or more of a shaft, an actuator, an actuator handle, a shaft handle, a vent, and a filament stop. The device may be used to mechanically push objects, as in retinal detachment repair, gasp objects, as in the removal of a dislocated intraocular lens or an intraocular foreign body, aspirate fluid, and cut materials, such as intraocular fragments.

13 Claims, 5 Drawing Sheets

(51) Int. Cl.
*A61B 18/00* (2006.01)
*A61B 18/08* (2006.01)
*A61B 18/14* (2006.01)
*A61B 18/20* (2006.01)
*A61B 90/00* (2016.01)
*A61F 9/007* (2006.01)
*A61F 9/008* (2006.01)
*A61B 17/3205* (2006.01)

(52) U.S. Cl.
CPC ...... *A61F 9/00727* (2013.01); *A61F 9/00821* (2013.01); *A61B 18/20* (2013.01); *A61B 2018/00154* (2013.01); *A61B 2018/00321* (2013.01); *A61B 2018/00589* (2013.01); *A61B 2018/00595* (2013.01); *A61B 2018/141* (2013.01); *A61B 2090/3925* (2016.02); *A61B 2090/3966* (2016.02); *A61B 2218/007* (2013.01); *A61F 2/1662* (2013.01); *A61F 9/007* (2013.01); *A61F 2009/00863* (2013.01); *A61F 2009/00874* (2013.01)

(58) Field of Classification Search
CPC .... A61F 2/1662; A61F 2/1664; A61B 18/082; A61B 18/085; A61B 18/20; A61B 17/32056; A61B 17/320708; A61B 17/320725; A61B 2017/320733; A61B 2017/320741; A61B 2090/3925; A61B 2090/3966; A61B 2009/00874; A61B 2009/00863; A61B 2018/00154; A61B 2018/00321; A61B 2018/00589; A61B 2018/00595; A61B 2018/1407; A61B 2218/007; A61B 2218/141
See application file for complete search history.

(56) References Cited

U.S. PATENT DOCUMENTS

| | | | | |
|---|---|---|---|---|
| 4,530,359 A | * | 7/1985 | Helfgott | A61F 9/00754 30/362 |
| 4,538,611 A | | 9/1985 | Kelman | |
| 4,732,150 A | | 3/1988 | Keener, Jr. | |
| 5,171,314 A | | 12/1992 | Dulebohn | |
| 5,417,684 A | * | 5/1995 | Jackson | A61B 17/00234 606/1 |
| 5,501,692 A | * | 3/1996 | Riza | A61B 17/0469 112/169 |
| 5,669,923 A | * | 9/1997 | Gordon | A61B 10/0266 604/22 |
| 2004/0024412 A1 | * | 2/2004 | Clements | A61M 5/155 606/107 |
| 2008/0183199 A1 | | 7/2008 | Attinger | |
| 2009/0054904 A1 | * | 2/2009 | Holmen | A61B 17/320016 606/107 |
| 2010/0179544 A1 | | 7/2010 | Bookhny et al. | |
| 2012/0158027 A1 | * | 6/2012 | Moradian | A61F 9/00754 606/166 |

FOREIGN PATENT DOCUMENTS

| | | |
|---|---|---|
| JP | 2008183407 | 8/2008 |
| JP | 6253652 | 11/2015 |
| WO | 2011106781 | 9/2011 |
| WO | 2011116228 | 9/2011 |

OTHER PUBLICATIONS

International Preliminary Report on Patentability dated Mar. 3, 2015 in Application No. PCT/US2013/056573.
Examination Report dated Jan. 20, 2016 in UK Application No. GB1503268.3.
Examination Report dated May 10, 2016 in UK Application No. GB1604731.8.
Office Action dated Mar. 28, 2017 in Japanese Application No. 2015-529887.
Examination Report dated Jan. 31, 2017 in UK Application No. GB1604731.8.
Examination Report dated Nov. 18, 2016 in UK Application No. GB1604731.8.
Examination Report dated Mar. 19, 2015 in UK Application No. GB1503268.3.

* cited by examiner

OPHTHALMIC SURGICAL DEVICE WITH ADJUSTABLE FILAMENT AND METHOD OF USE

FIELD OF INVENTION

The present disclosure relates to manipulating objects and materials in the eye.

BACKGROUND OF THE INVENTION

In repairing retinal detachments, a heavy liquid perfluorocarbon may be required in order to reattach the retina so that laser photocoagulation, diathermy, or cryotherapy can be applied to create a bond between the retina and the eye wall, preventing recurrence of the detachment. Perfluorocarbons are expensive and, if left in the eye (e.g., trapped beneath the retina), can be toxic and/or disrupt normal retinal electrophysiology. Further, during small-gauge surgery using surgical entry ports, there is often a difficulty injecting the perfluorocarbon into the eye because of the increased pressure, which can interrupt flow to the central retinal artery, placing the patient's vision at risk. Alternately, a drainage hole, called a posterior retinology in the retina can be made, through which subretinal fluid can be drained in order to reattach the retina with laser photocoagulation. However, creating an additional hole in the retina creates a permanent blind spot in the patient's vision, and can increase the chances of a recurrent retinal detachment.

In other instances, an implanted intraocular lens may dislocate within the eye, such that it falls completely back into the vitreous cavity, or is partially dislocated. Surgery is often required to retrieve these lenses so that they can be affixed into place, or replaced with another lens. However, available microforceps are often inadequate to manipulate the dislocated lens. Often, the forceps may break the lens haptic from the optic during surgery, or leave marks on the optic degrading its optical qualities.

In yet other instances, an eye may be injured with a foreign body during an accident. Oftentimes these are irregularly shaped pieces of metal, glass, ceramic, or other hard materials. Conventional forceps are often inadequate for grasping, removing and manipulating these irregularly shaped, foreign bodies securely during surgery to repair the eye.

Further, intraocular fragments (e.g., retained lens fragments following cataract surgery) may require removal with a phacoemulsification machine. Phacoemulsification hand pieces require large amounts of electrical power and a larger wound to remove intraocular fragments, and because of their high vacuum, may inadvertently pull on the vitreous body and cause retinal tears and detachments.

Thus, there exists a need in the art for the present ophthalmic surgical device with adjustable filament and method of use.

SUMMARY OF THE INVENTION

An ophthalmic surgical device in accordance with various embodiments of the present disclosure comprises an elongate element and a filament. The device may further comprise one or more of a shaft, an actuator, an actuator handle, a shaft handle, a vent, and a filament stop. The device may be used to mechanically push objects, as in retinal detachment repair, grasp objects, as in the removal of a dislocated intraocular lens or an intraocular foreign body, aspirate fluid, and cut materials, such as intraocular lens fragments.

BRIEF DESCRIPTION OF THE DRAWINGS

The accompanying drawings are included to provide a further understanding of the disclosure and are incorporated in and constitute a part of this specification, illustrate embodiments of the disclosure, and together with the description serve to explain the principles of the disclosure.

DETAILED DESCRIPTION

Figure 1:
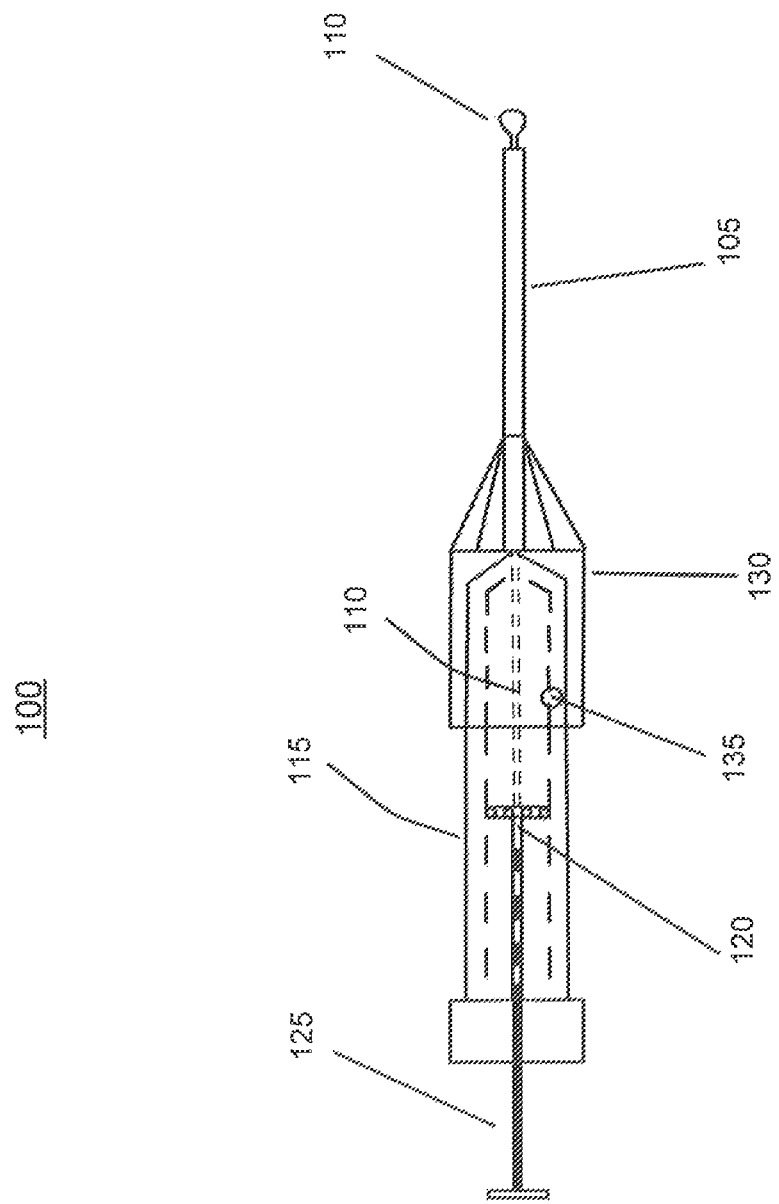
FIG. 1 illustrates an ophthalmic surgical device in accordance with various embodiments of the present disclosure.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "proximal" and "distal," when used herein in relation to a device or device component, refer respectively, to directions closer to and farther away from the device's operator.

An ophthalmic surgical device in accordance with various embodiments of the present disclosure may be used to mechanically push objects, as in retinal detachment repair, grasp objects, as in the removal of a dislocated intraocular lens or an intraocular foreign body, aspirate fluid, and cut materials, such as intraocular lens fragments.

The device of the present disclosure can be particularly useful in ophthalmic surgeries and procedures including securement in iris defects, securing or fixing in place intraocular implants such as intraocular lenses, glaucoma tube shunts, implantable hardware for the eye, securing full and partial thickness cornea transplants, LASIK and DSEK/DLEK flaps, temporary and permanent keratoprostheses, implantable ocular lenses, contact lenses and telescopic lenses, presbyopia reversal, scleral patch grafts and scleral rings, conjunctival and amniotic membrane grafts, repair of the iris and iris root defects, iridoplasty, pupiloplasty, securing dislocated intraocular lenses to the iris, anchoring the capsular bag, anchoring capsular tension rings, corneal wound closure, anchoring tube shunts both in the anterior chamber and externally to the sclera, closure of sclerotomies, conjunctival flaps, trabeculotomy and trabeculectomy blebs, closure of cyclodialysis clefts, fixation of intraocular pressure monitoring devices, fixation of intraocular implants for sustained drug delivery, anchoring orbital reconstruction hardware, weighted lid implants, eyelid skin and muscle wound closure, fixation of lacrimal system hardware, tarsorraphy, repair of ptosis, blepharoplasty, correction of entropion and ectropion, canthoplasty, fixation of virectomy infusion line, closure of sclerotomies, scleral buckling with or without silicone band or sponge hardware, retinopexy, closure of traumatic corneal and scleral wounds, fixation of radioactive plaques for the treatment of intraocular tumors, fixation of intraocular hardware and implantable chips for artificial vision and electrical stimulation of the retina, correction of blepharospasm, and fixation of extraocular muscles to sclera for resection, recession, and transposition surgeries.

With reference now to FIG. 1, an ophthalmic surgical device 100 in accordance with various embodiments of the present disclosure comprises an elongate element 105 through which a filament 110 can be deployed and/or retracted. Device 100 may further comprise one or more of a shaft 115 coupled to elongate element 105, an actuator 120 coupled to filament 110, an actuator handle 125 coupled to actuator 120, a shaft handle 130 coupled to shaft 115 and/or elongate element 105, a vent 135, and a filament stop 140 (see, FIG. 2).

Elongate element 105 is generally any longitudinally extending structure with a lumen extending therethrough. Thus, elongate element 105 can be a cannula, needle, trocar, introducer, or the like. A sharp tip, hallow bore needle can be used to penetrate tissue directly without the need for a separate surgical wound or trocar. Nevertheless, it will be evident to those skilled in the art that the tip of elongate element 105 can be either dull or sharp. Elongate element 105 can be any material and can have any cross-sectional shape including, but not limited to, profiles that are elliptical (e.g., circles, ellipses, and the like), non-elliptical (e.g., triangles, rectangles, squares, hexagons, trapezoids, pentagons, stars, and the like), or random. Moreover, the cross-section can vary in shape and/or size from end to end. In various embodiments, elongate element 105 has a small crossing profile, for example less than about 25 gauge, about 20 gauge, or smaller. The length of elongate element 105 can be selected by the user for a particular procedure, yet may be from about 1.0 cm to about 30.0 cm in example embodiments.

Filament 110 can be deployed and/or retracted through elongate element 105. In various embodiments, filament 110 comprises a shape-memory material, such as nitinol or the like that has been heat treated to a desired configuration. In other embodiments, filament 110 comprises a resilient material such as stainless steel, nylon, polypropylene, or another metallic or polymeric material. In other embodiments, the material may be a shape-memory polymer, plastic, or metal or biomaterial, with either biodegradable or non-biodegradable characteristics.

In general, filament 110 is capable of elastic deformation. In this regard, filament 100 can have a linear configuration when retracted within elongate element 105, and resume a non-linear configuration when deployed from elongate element 105. Such a non-linear configuration can be a loop, circle, hook, or any other 1, 2, or 3-dimensional configuration deemed useful by a user to mechanically push objects, grasp objects, or cut materials.

In various embodiments, filament 110 is biocompatible. In various embodiments, filament 110 has a thickness of less than about 1.0 mm, about 0.5 mm, or smaller.

In various embodiments, electric current can be passed through one or more filaments 110, allowing the user to apply local cautery to tissue. Similarly, heat can be passed through one or more filaments 110 to cauterize tissue. Filament 110 can be coated with one or more of a radiopaque material, an echogenic material, and a therapeutic agent.

Device 100 can further comprise a shaft 115 coupled to elongate element 105. In an example embodiment, a distal end of shaft 115 is coupled to a proximal end of elongate element 105. In an example embodiment, shaft 115 comprises a syringe. Shaft 115 can be in sealed, or substantially sealed, communication with elongate element 105. In this regard, a fluid and/or a gas can pass between shaft 115 and elongate element 105, without loss of volume or pressure along the way. Elongate element 105 can connect to shaft 115 in a manner similar to a standard syringe via threads or a twist lock (e.g., a liter lock type fitting).

In various embodiments, device 100 further comprises a shaft handle 130 coupled to shaft 115 and/or elongate element 105, in an example embodiment, an inner surface of shaft handle 130 is coupled to an outer surface of shaft 115 and/or an outer surface of elongate element 105. Elongate element 105 and shaft handle 130 can be one single piece. Shaft 115 and shaft handle 130 can also be one single piece.

In various embodiments, shall handle 130 can be configured to allow a user to control and/or manipulate shaft 115. Shaft handle 130 can be further configured to provide for ergonomic use. In one example embodiment, shaft handle 130 comprises a finger support (not shown). The finger support may comprise a single opening or two openings on opposite sides of shaft 115 for inserting a user's finger(s) therethrough.

Device 100 can further comprise an actuator 120 coupled to one or more ends of filament 110. Such coupling may be permanent or temporary. In this regard, actuator 120 can be configured to allow a user to deploy and/or retract filament 110 through elongate element 105. In various embodiments, a single filament is loaded into elongate element 105 and deployed using actuator 120. By way of example, filament 110 can comprises a loop located at or proximal to a distal opening of elongate element 105, wherein the ends of the loop extend back into elongate element 105 and are coupled to actuator 120. In various other embodiments, two or more filaments 110 can be hack loaded into elongate element 105 and deployed using actuator 120.

Actuator 120 can be configured to slide freely within shaft 115. In various embodiments, actuator 120 is configured to slide sealingly within shaft 115, as a "plunger," to advance and/or uptake a fluid and/or gas through shaft 115 and elongate element 105. Notwithstanding the foregoing, it will be evident to those skilled in the art that actuator 120 could be replaced with a button or other mechanical device which would cause filament 110 to deploy and/or retract through elongate element 105.

In one illustrative embodiment, actuator 120 is configured to anchor a proximal end of one or more filaments 110, for example, by frictional engagement, mechanical engagement, adhesion, etc. In this manner, actuator 120 may be configured to deploy one or more filaments 110 from device 100 once in a desired position. Similarly, actuator 120 may be configured to retract one or more filaments 110 if necessary.

In various embodiments, device 100 further comprises an actuator handle 125 coupled to actuator 120. Actuator 120 can connect to actuator handle 125 in a manner similar to a standard syringe via threads or a twist lock (e.g., a luer lock type fitting). Moreover, any suitable connection type may be used between actuator 120 and actuator handle 125. In another example embodiment, actuator 120 and actuator handle 125 can be one single piece.

In various embodiments, actuator handle 125 can be configured to allow a user to control and/or manipulate actuator 120. Actuator handle 125 can be further configured to provide for ergonomic use. In one example embodiment, actuator handle 125 comprises a thumb support (not shown). The thumb support may comprise a post or include an opening for inserting a user's thumb therethrough.

In example embodiments, actuator 120 can comprise a geared or ratcheted system that deploys filament 110 by either rotation of actuator 120 or compression of a button or lever. In other example embodiments, actuator 120 can comprise a system that deploys filament 110 by twisting, wheeled action or sliding. Alternatively, in yet another illustrative embodiment, actuator 120 may comprise a pneumatically driven system or a hydraulically driven system such as those currently known in the art, and configured to control deployment of filament 110. In yet another illustrative embodiment, actuator 120 of the present disclosure may be capable of interfacing with a foot pedal or a trigger device configured to control deployment of filament 110.

In another illustrative embodiment of device 100, device 100 may include a mechanism capable of retracting filament 110 from the body. In yet another illustrative embodiment, actuator 120 of the present disclosure can be a viscoelastic material that is configured to deploy filament 110.

In an example embodiment, device 100 further comprises a vent 135. In general, vent 135 comprises a conduit or passageway through one or both of shaft handle 130 and shaft 115, and into the interior lumen of shaft 115. Vent 135 can be in sealed, or substantially sealed, communication with one or both of shaft handle 130 and shaft 115, in this regard, a fluid and/or a gas can pass between vent 135 and a distal opening of elongate element 105, without loss of volume or pressure along the way.

Vent 135 can be left open (or not closed) to introduce a fluid and/or gas to into shaft 115 and elongate element 105. Vent 135 can be left, open (or not closed) by a user's finger, a stopper, a valve, or the like, Vent 135 may be useful en example embodiments wherein actuator 120 is configured to slide sealingly within shaft 115, as a "plunger," to advance and/or uptake a fluid and/or gas through shaft 115 and elongate element 105, as described above.

In other example embodiments, vent 135 can comprise a coupling (e.g., a luer lock type fitting) to attach an external fluid and/or gas supply, for example a suction line, providing active aspiration during surgery. Notwithstanding the foregoing, it will be evident to those skilled in the art that an external fluid and/or gas can be applied passively, in addition to actively.

Figure 2:
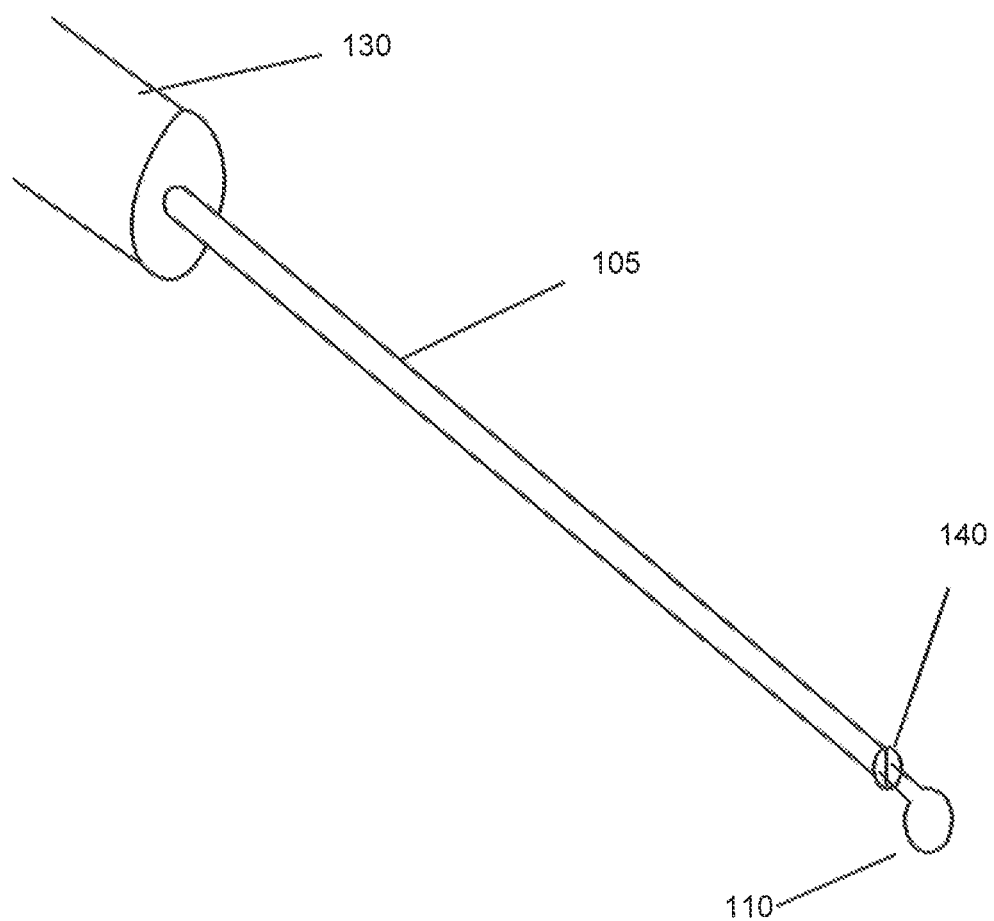
FIG. 2 illustrates a filament stop of an ophthalmic surgical device in accordance with various embodiments of the present disclosure.

With reference now to FIG. 2, device 100 can further comprise a filament stop 140. In various embodiments, filament stop 140 is located at or proximal to a distal opening of elongate element 105, and is generally configured to prevent filament 110 from fully retracting back into elongate element 105. In one such embodiment, filament stop 140 comprises a small strip of material extended across a distal opening of elongate element 105, for example stainless steel, nylon, polypropylene, or another metallic or polymeric material. In general, filament stop 140 is configured to physically a portion of filament 110, and prevent its passage back into elongate element 105. In an example, embodiment, filament 110 comprises a loop, wherein the ends of the loop extend back into elongate element 105 on either side of filament stop 140.

Notwithstanding the foregoing, it will be evident to those skilled in the art that filament stop 140 can be eliminated to allow filament 110 to completely retract back into elongate element 105.

Figure 3A:
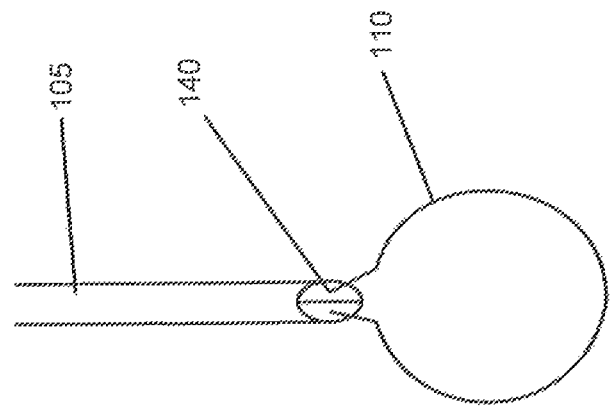
FIGS. 3A-3C progressively illustrate deployment of a filament from an ophthalmic surgical device in accordance with various embodiments of the present disclosure.
Figure 3B:
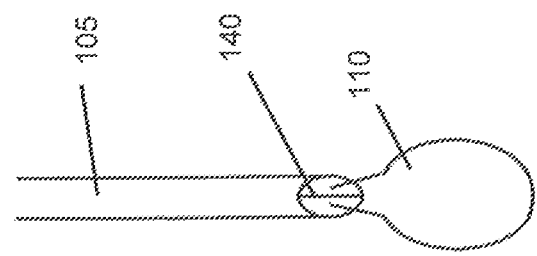
Figure 3C:
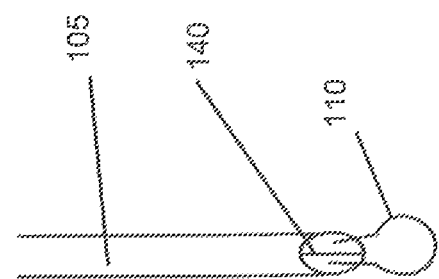

Turning to FIGS. 3A-3C, upon sliding actuator 120 towards the distal end of elongate element 105, filament 110 is deployed out of the tip of elongate element 105, allowing filament 110 to transform from its linear configuration to its non-linear (e.g., shape-memory) configuration. Upon sliding actuator 120 away from the distal end of elongate element 105, filament 110 is retracted back into elongate element 105, with filament stop 140 being generally configured to prevent filament 110 from fully retracting back into elongate element 105.

In an illustrative embodiment, device 100 requires no electrical power. For example, device 100 may be entirely manually actuated. In another illustrative embodiment, device 100 of the present disclosure may be capable of interfacing with a robotic arm for remote or telescopic surgery. In various example embodiments, relative movement of actuator 120 could be pneumatic, electric, or hydraulic in nature.

Methods of use are also provided for herein. In various embodiments of the present disclosure, filament 110 is in a linear configuration inside the lumen of elongate element 105. Elongate element 105 is then passed into the eye through a surgical opening, sclerotomy, corneal wound, port, cannula, needle, trocar, introducer, or other opening. Once inside the eye, actuator 120 is used to deploy filament 110 from the lumen of elongate element 105. After deployment, filament 110 returns to its non-linear configuration. In some embodiment, this non-linear configuration may be a loop.

Figure 4:
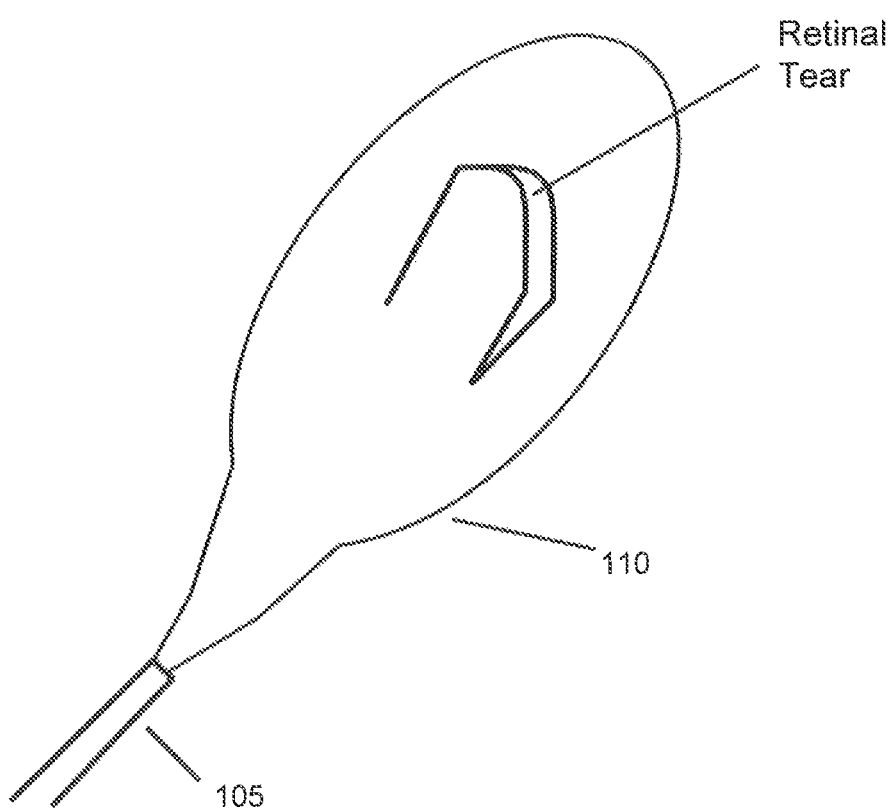
FIG. 4 illustrates a method of use in accordance with various embodiments of the present disclosure.
Figure 5:
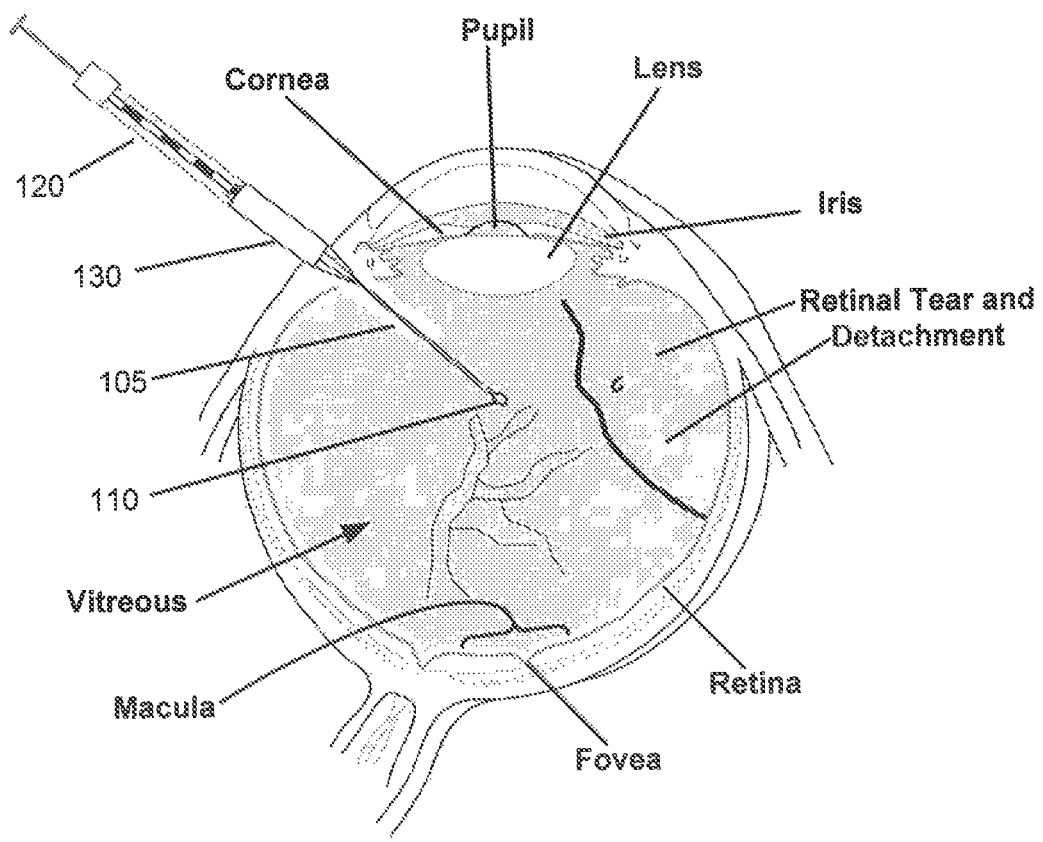
FIG. 5 illustrates a method of use in accordance with various embodiments of the present disclosure.

In one aspect of an embodiment of the present disclosure, and with reference with FIGS. 4 and 5, the loop that is filament 110 can be used in connection with retinal detachment repair during a vitrectomy. The abovementioned loop is placed over a retinal detachment in the area of a retinal tear. The loop is then used to mechanically push the retina back against the eye wall. During this step, the subretinal fluid can be drained from the subretinal space through the lumen of elongate element 105 and egress through vent 135. This can be accomplished by providing active aspiration at vent 135 and/or upon sliding actuator 120 away from the distal end of elongate element 105 to create negative pressure within the lumen of shaft 115. This causes the retina to reattach. Once the retina is reattached, a laser endoprobe (not shown) can be used to apply photocoagulation around the retinal tear, reattaching the retina. In an example embodiment, the above described retinal detachment repair is performed without heavy perfluorocarbon liquids or a posterior drainage retinotomy. Alternatively, the filament may be heated, cooled, or used to conduct electricity or induce cautery in order to seal the retinal tear without the need for laser.

In another aspect of an embodiment of the present disclosure, the loop that is filament 110 can be used in connection with the removal of a dislocated intraocular lens or an intraocular foreign body during a vitrectomy. In this example embodiment, after deployment of the filament in a loop or similar shape, the loop is placed around the item, and then filament 110 is retracted like a snare by retracting actuator 120. In this example embodiment, filament 110 is configured to grasp and assist with the removal from the eye of the dislocated intraocular lens or intraocular foreign body during a vitrectomy.

In yet another aspect of an embodiment of the present disclosure, the loop that is filament 110 can be used in connection with cutting intraocular fragments. The above-mentioned loop is used to grasp intraocular fragments (e.g., retained lens fragments following cataract surgery). Actuator 120 is then used to retract filament 110 back into elongate element 105, causing the intraocular fragments to be cut. Actuator 120 is then used to re-deploy filament 110, and the process is repeated as many times as necessary to reduce the intraocular fragments to such a size that they can be removed with a vitreous cutter or simple aspiration, without the need for phacoemulsification. Alternatively, the filament may be heated, cooled, or used to conduct electricity or induce cautery in order to facilitate removal of the lens fragments without the need for phacoemulsification.

It will be apparent to those skilled in the art that various modifications and variations can be made in the present disclosure without departing from the spirit or scope of the disclosure. Thus, it is intended that the embodiments described herein cover the modifications and variations of this disclosure provided they come within the scope of the appended claims and their equivalents.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications can be made, especially in matters of structure, materials, elements, components, shape, size and arrangement of parts including combinations within the principles of the invention, to the full extent indicated by the broad, general meaning of the terms in which the appended claims are expressed. For example, while the present disclosure has been described primarily with reference to pushing objects, grasping objects, and cutting materials in the eye, all objects and materials (whether in the eye or not) are within the scope of the present disclosure. To the extent that these various modifications do not depart from the spirit and scope of the appended claims, they are intended to be encompassed therein.

The invention claimed is:

1. An ophthalmic surgical device comprising:
    a filament comprising a proximal portion and a distal portion,
    an elongate element through which the filament can be retracted and deployed, the elongate element comprising a proximal opening and a distal opening,
    a shaft coupled to the elongate element at the proximal opening,
    a vent extending through the shaft, wherein the vent is in fluid communication with the elongate element via the proximal opening of the elongate element, and
    an actuator permanently coupled to the proximal portion of the filament, wherein the actuator is configured to slide freely within the shaft,
    wherein the distal portion of the filament has a linear configuration when retracted within the elongate element, and the distal portion of the filament has a non-linear configuration when deployed from the distal opening of the elongate element; and
    wherein the vent is configured to permit at least one of a fluid and a gas to pass between the vent and the distal opening of the elongate element, via the proximal opening of the elongate element, when the distal portion of the filament is deployed from the distal opening of the elongate element and when the distal portion of the filament is retracted within the distal opening of the elongate element,
    wherein the vent is in sealed communication with the shaft and the elongate element such that the fluid or the gas can pass between the vent and the distal opening of the elongate element, without loss of volume or pressure along the way.

2. The ophthalmic surgical device of claim 1, wherein the elongate element is a cannula having a sharp tip.

3. The ophthalmic surgical device of claim 1, wherein the filament comprises a shape-memory material.

4. The ophthalmic surgical device of claim 3, wherein the shape-memory material is nitinol.

5. The ophthalmic surgical device of claim 1, wherein the non-linear configuration is a loop.

6. The ophthalmic surgical device of claim 1, further comprising:
    an actuator handle coupled to the actuator, and
    a shaft handle coupled to the shaft or the elongate element.

7. The ophthalmic surgical device of claim 6, wherein the actuator handle comprises a thumb support.

8. The ophthalmic surgical device of claim 6, wherein the shaft handle comprises a finger support.

9. The ophthalmic surgical device of claim 6, further comprising a filament stop that is configured to prevent the filament from fully retracting back into the elongate element.

10. An ophthalmic surgical device comprising:
    a shaft defining an internal chamber and a vent, wherein the vent extends through the shaft and is open to the internal chamber, wherein the shaft comprises a distal end;
    an elongate element comprising a proximal opening and a distal opening, wherein the distal end of the shaft is coupled to the elongate element at the proximal opening such that the proximal opening is open to the internal chamber;
    an actuator coupled to the shaft and comprising a portion that is configured to slide freely within the internal chamber of the shaft; and
    a filament configured to be retracted and deployed through the elongate element in response to movement of the actuator, wherein the filament comprises a proximal portion and a distal portion, wherein the proximal portion is coupled to the actuator, wherein the distal portion of the filament has a non-linear configuration when deployed from the distal opening of the elongate element and the distal portion of the filament has a linear configuration when retracted within the distal opening of the elongate element,
    wherein the vent is configured to permit at least one of a fluid and a gas to pass between the vent and the distal opening of the elongate element, via the proximal opening of the elongate element, with the filament movably disposed within the elongate element.

11. The ophthalmic surgical device of claim 10, wherein the vent is configured to permit the at least one of the fluid and the gas to pass between the vent and the distal opening of the elongate element, via the proximal opening of the elongate element, regardless of whether the distal portion of the filament is deployed from the distal opening of the elongate element or whether the distal portion of the filament is retracted within the distal opening of elongate element.

12. The ophthalmic surgical device of claim 10, wherein the vent comprises a coupling for attaching at least one of an external fluid source and a suction source to the shaft such that at least one of fluid and suction, respectively, is configured to be provided to the internal chamber of the shaft.

13. The ophthalmic surgical device of claim 12, wherein the suction source is at least one active or passive.

* * * * *